United States Patent [19]

Iwane et al.

[11] Patent Number: 5,344,969
[45] Date of Patent: Sep. 6, 1994

[54] PROCESS FOR PURIFICATION OF NAPHTHALENEDICARBOXYLIC ACID

[75] Inventors: Hiroshi Iwane; Takahiro Sugawara; Miwa Shirasaki, all of Ibaraki, Japan

[73] Assignee: Mitsubishi Petrochemical Co., Ltd., Tokyo, Japan

[21] Appl. No.: 983,411

[22] Filed: Nov. 30, 1992

[30] Foreign Application Priority Data

Dec. 3, 1991 [JP] Japan .................................. 3-319426
Apr. 22, 1992 [JP] Japan .................................. 4-102833

[51] Int. Cl.$^5$ ............................................ C07C 51/43
[52] U.S. Cl. ................................... 562/486; 562/412
[58] Field of Search ........................................ 562/486

[56] References Cited

U.S. PATENT DOCUMENTS 2,849,483  8/1958  Ham .
2,949,483  8/1960  Ham .

FOREIGN PATENT DOCUMENTS 50-142542  11/1975  Japan .

Primary Examiner—José Dees
Assistant Examiner—Vera C. Clarke
Attorney, Agent, or Firm—Oblon, Spivak, McClelland, Maier & Neustadt

[57] ABSTRACT

A process for purifying a crude naphthalenedicarboxylic acid containing impurities and coloring substances obtained by the oxidation of a di-substituted naphthalene, dispense with the use of a large amount of alkali or acid, and producing a naphthalenedicarboxylic acid having a high purity and good color effectively and in a high recovery is disclosed, which comprises dissolving the crude naphthalenedicarboxylic acid in a mixed solvent comprising an amine compound and an alcohol and conducting crystallization.

16 Claims, No Drawings

PROCESS FOR PURIFICATION OF NAPHTHALENEDICARBOXYLIC ACID

FIELD OF THE INVENTION

The present invention relates to a process for producing a naphthalenedicarboxylic acid.

Naphthalenedicarboxylic acids are compounds useful as, for example, raw materials for high-performance resins such as poly(ethylene naphthalate) (PEN resins).

BACKGROUND OF THE INVENTION

In general, naphthalenedicarboxylic acids are produced by a method in which substituted naphthalenes having two substituents each capable of being converted into a carboxyl group through oxidation reaction, e.g., di-alkyl-substituted naphthalenes such as dimethylnaphthalenes and diisopropylnaphthalenes, are oxidized with molecular-state oxygen in the presence of cobalt, manganese, and bromine. Since the crude naphthalenedicarboxylic acids obtained by this method contain impurities, e.g., trimellitic acid, and coloring substances, a purifying step is necessary.

A conventionally known purification method for naphthalenedicarboxylic acids comprises dissolving a crude naphthalenedicarboxylic acid in an aqueous solution of an alkali, subjecting the solution to such treatments as oxidation, hydrogenation, decoloring by adsorption, etc., and then acidifying the resulting solution, thereby to obtain the naphthalenedicarboxylic acid having a high purity (JP-A-48-68554, JP-B-52-20993, JP-A-50-105639, JP-A-50-160248 and others). (The terms "JP-A" and "JP-B" as used herein mean an "unexamined published Japanese patent application" and an "examined Japanese patent publication", respectively.)

However, the above method has had a problem that because an alkali and an acid are used in large quantities, an inorganic salt is produced and wastewater is discharged in large quantities.

On the other hand, JP-A-62-230747 discloses a purification method which comprises dissolving a crude naphthalenedicarboxylic acid in an organic solvent selected from N,N-dimethylformamide (DMF), N,N-dimethylacetamide (DMAc), and dimethyl sulfoxide (DMSO), treating the solution with active carbon, and then recrystallizing the naphthalenedicarboxylic acid.

The above method, however, has a drawback that due to the low solubilities of naphthalenedicarboxylic acids in DMF or DMSO, the solvent should be used in a large amount. Further, it has been found, from purification experiments conducted by the present inventors according to the above method, that when a purified naphthalenedicarboxylic acid is obtained in such a manner as to result in a higher recovery, almost no improvement is attained in the color of the compound (see Comparative Examples 6 and 7). In addition, the above method has had a further problem that those organic solvents are difficult to recover because of their high boiling points and are highly toxic.

JP-A-50-142542 discloses a purification method which comprises dissolving crude 2,6-naphthalenedicarboxylic acid in an aqueous solution of a specific alkylamine, e.g., dimethylamine, and then removing the amine from the solution by distillation thereby to precipitate the 2,6-naphthalenedicarboxylic acid.

However, the above purification method has had drawbacks such as the following: (1) amines usable in the method are limited to those which can be easily distilled, because in order to precipitate the naphthalenedicarboxylic acid, the amines should be removed and recovered by distillation; (2) a large proportion of the water in the aqueous solution is lost along with the amine since the amine evaporates as a boiling mixture with water; and (3) the recovery attainable by the method is low because complete removal of the amine from the aqueous solution is impossible.

SUMMARY OF THE INVENTION

An object of the present invention is to provide a process for producing, in a high recovery, a naphthalenedicarboxylic acid having a high purity and good color.

Other objects and effects of the present invention will be apparent from the following description.

The process of the present invention for producing a naphthalenedicarboxylic acid comprises dissolving a crude naphthalenedicarboxylic acid in a mixed solvent comprising an amine compound and an alcohol and conducting crystallization, the crude naphthalenedicarboxylic acid being one obtained by the oxidation of a di-substituted naphthalene.

DETAILED DESCRIPTION OF THE INVENTION

Di-Substituted Naphthalene

The di-substituted naphthalene to be used for producing a crude naphthalenedicarboxylic acid purified in the process of the present invention has two substituents which each is capable of being converted into a carboxyl group through oxidation reaction. Examples of such substituents include an alkyl group, an acyl group, a formyl group, a hydroxyalkyl group, and a hydroperoxyalkyl group.

The positions of the two substituents are not particularly limited. It is, however, preferable that the two substituents be not bonded to any adjacent two carbon atoms, specifically, not bonded at the 1,2-positions or the 2,3-positions. Especially preferred examples of the substitution positions are the 2,6-positions and the 2,7-positions.

Crude Naphthalenedicarboxylic Acid

The crude naphthalenedicarboxylic acid to be purified by the present invention may be obtained by oxidizing the above-described di-substituted naphthalene with molecular-state oxygen, e.g., the oxygen in air, in a solvent, e.g., an aliphatic lower monocarboxylic acid or water, in the presence of a catalyst, e.g., one comprising heavy metals and bromine.

Examples of the aliphatic lower monocarboxylic acid as a solvent for the di-substituted naphthalene include formic acid, acetic acid, propionic acid, butyric acid, valeric acid, and bromoacetic acid. Of these, acetic acid is most preferred. The monocarboxylic acid may be used after being diluted with other solvent such as water or an aromatic hydrocarbon.

The amount of the solvent to be used is not particularly limited, but it is preferably from 0.5 to 10 times by weight, more preferably from 1 to 6 times by weight, the amount of the di-substituted naphthalene used as a raw material.

As the heavy metals for use as a component of the catalyst, a combination of a cobalt compound and a manganese compound or the like may be employed.

Examples of such heavy metal compounds include cobalt and manganese salts of various acids such as aliphatic carboxylic acids, e.g., formic acid, acetic acid, propionic acid, oxalic acid, and maleic acid, alicyclic carboxylic acids, e.g., naphthenic acid, and aromatic carboxylic acids, e.g., benzoic acid, terephthalic acid, naphthoic acid, and naphthalenedicarboxylic acid, and inorganic salts of cobalt and manganese such as the hydroxides, oxides, carbonates, and halides of the metals. Preferred of these are the acetates and bromides.

Such a cobalt compound and manganese compound may be used as a mixture thereof in such a proportion that the cobalt:manganese ratio (atomic ratio) is generally in the range of from 99:1 to 1:99, preferably from 97:3 to 3:97.

The amount of a cobalt compound and manganese compound to be used as a catalyst component is generally in the range of from 0.01 to 10% by weight, preferably from 0.2 to 5% by weight, in terms of the total amount of cobalt atoms and manganese atoms based on the amount of an aliphatic carboxylic acid used as the solvent.

The bromine as a component of the catalyst for use in producing a crude naphthalenedicarboxylic acid may be molecular-state bromine or in the form of a bromine compound. Examples of the bromine compound include inorganic bromine compounds such as hydrogen bromide, bromides of alkali metals, bromides of alkaline earth metals, and salts of hydrobromic acid and organic bromine compounds such as methyl bromide, ethyl bromide, bromoform, ethylene bromide, and bromoacetic acid.

Such a bromine compound or molecular-state bromine may be used in such an amount that the amount of bromine atoms present in the reaction system is generally in the range of from 0.1 to 10 times by mol, preferably from 0.2 to 5 times by mol, the sum of the cobalt atoms and manganese atoms contained in an aliphatic carboxylic acid used as the solvent.

The oxidation reaction is conducted at a temperature of usually from 100° to 300° C., with the oxygen partial pressure in the gas phase being preferably from 0.2 to 10 kg/cm$^2$ in terms of absolute pressure.

After completion of the reaction, the reaction mixture is cooled to around room temperature and the precipitated solid is recovered, thereby obtaining a crude naphthalenedicarboxylic acid. The thus-obtained crude naphthalenedicarboxylic acid has a purity of 90% or more, in most cases in the range of from 95 to 99%, and is usually of a pale yellow to brown color. This crude compound may then be subjected as it is to the crystallizing step according to the present invention, or may be subjected to the crystallization after being washed with a reaction solvent or other liquid. If required and necessary, the purity of the crude naphthalenedicarboxylic acid may be heightened to 99% or more by treatment with active carbon, DMSO, etc., before the crude compound is subjected to crystallization, thereby to impart an improved color no the crystallized compound to be obtained.

Amine Compound

Examples of the amine compound for use in the mixed solvent for crystallization in the process of the present invention include aliphatic amines such as methylamine, dimethylamine, trimethylamine, ethylamine, diethylamine, triethylamine, n-propylamine, di-n-propylamine, trin-n-propylamine isopropylamine, diisopropylamine, triisopropylamine, n-butylamine, di-n-butylamine, tri-n-butylamine, sec-butylamine, di-sec-butylamine, tri-sec-butylamine, tert-butylamine, di-tert-butylamine, tri-tert-butylamine, n-hexylamine, di-n-hexylamine, tri-n-hexylamine, cyclohexylamine, dicyclohexylamine, tricyclohexylamine, n-octylamine, di-n-octylamine, tri-n-octylamine, ethylenediamine, N-methylethylenediamine, N,N-dimethylethylenediamine, N,N'-dimethylethylenediamine, N,N,N'-trimethylethylenediamine, N,N,N',N'-tetramethylethylenediamine, 1,2-diaminopropane, 1,3-diaminopropane, N-methyl-1,2-diaminopropane, N-methyl-1,3-diaminopropane, N,N-dimethyl-1,2-diaminopropane, N,N-dimethyl-1,3-diaminopropane, N,N,N'-trimethyl-1,2-diaminopropane, N,N,N'-trimethyl-1,3-diaminopropane, N,N,N',N'-tetramethyl-1,2-diaminopropane, N,N,N',N'-tetramethyl-1,3-diaminopropane, monoethanolamine, diethanolamine, triethanolamine, and glycine; ammonium salts derived from these aliphatic amines; and alicyclic amines such as piperidine, N-methylpiperidine, hexamethyleneimine, and N-methylhexamethyleneimine. Preferred of these are alkylamines having up to 30 carbon atoms.

These amine compounds may be used either alone or as a mixture of two or more thereof in an arbitrary proportion.

Alcohol

Examples of the alcohol for use in the mixed solvent for crystallization in the process of the present invention include aliphatic monohydric alcohols such as methyl alcohol, ethyl alcohol, n-propyl alcohol, isopropyl alcohol, n-butyl alcohol, isobutyl alcohol, sec-butyl alcohol, tert-butyl alcohol, n-amyl alcohol, isoamyl alcohol, sec-amyl alcohol, tert-amyl alcohol, neopentyl alcohol, hexyl alcohol, pentyl alcohol, octyl alcohol, nonyl alcohol, and decyl alcohol; alicyclic monohydric alcohols such as cyclopentyl alcohol and cyclohexyl alcohol; aliphatic straight-chain diols such as ethylene glycol, 1,2-propylene glycol, and 1,3-propylene glycol; alicyclic diols such as 1,2-cyclopentanediol, 1,3-cyclopentanediol, 1,2-cyclohexanediol, 1,3-cyclohexanediol, and 1,4-cyclohexanediol; and aliphatic polyols such as glycerol and pentaerythritol. Preferred examples thereof include aliphatic monohydric alcohols having 3 or less carbon atoms and diols having 3 or less carbon atoms.

These alcohols may be used either alone or as a mixture of two or more thereof in an arbitrary proportion.

Mixed Solvent

In the process of the present invention, a crude naphthalenedicarboxylic acid is dissolved in a mixed solvent comprising an amine compound and alcohol such as those enumerated above, and the resulting solution is subjected to crystallization.

Preferred examples of the mixed solvent include those comprising aliphatic amines having up to 15 carbon atoms as the amine compound and aliphatic monohydric alcohols having 3 or less carbon atoms or diols having 3 or less carbon atoms as the alcohol.

The proportion of the amine compound to the alcohol in the mixed solvent may be generally in the range of from 1:99 to 99:1 by weight, preferably from 5:95 to 95:5 by weight.

The amount of the amine compound-alcohol mixed solvent to be used is not particularly limited as long as it is sufficient to dissolve the crude naphthalenedicarboxylic acid. The amount of the mixed solvent to be used cannot be fixed unconditionally because it varies depending on the proportion of the amine compound to the alcohol and on the temperature at which the crude naphthalenedicarboxylic acid is dissolved. Usually, however, the mixed solvent is used in an amount generally in the range of from 0.5 to 100 times by weight, preferably from 1 to 50 times by weight, the amount of the crude naphthalenedicarboxylic acid. If the amount of the mixed solvent used is below the lower limit specified above, a sufficient crystallizing effect cannot be obtained. Mixed solvent amounts exceeding the upper limit are not preferred in that even if the mixed solvent is used in such a large amount, the crystallizing effect cannot be heightened any more, only making the process uneconomical due to the use of an increased amount of the solvent.

Higher temperatures are preferred in dissolving the crude naphthalenedicarboxylic acid in the mixed solvent. Usually, however, the dissolution is conducted at a temperature in the range of from 0° to 350° C., preferably from 60° to 250° C. There are no particular limitations on pressure during the dissolution.

Crystallization Operation

The crystallization operation according to the present invention may be conducted as follows. First, a crude naphthalenedicarboxylic acid is dissolved in a predetermined amount of the mixed solvent. In the case where an insoluble matter is present in the resulting solution, it is removed by filtration. The solution of the crude naphthalenedicarboxylic acid may be treated with active carbon or the like. The treatment with active carbon may be carried out either by a batch-wise method in which a predetermined amount of active carbon is added to the mixed solvent solution of a crude naphthalenedicarboxylic acid and the resultant mixture is stirred with heating and then filtered, or by a continuous method in which the mixed solvent solution of a crude naphthalenedicarboxylic acid is passed through a column packed with active carbon.

If required and necessary, the crude naphthalenedicarboxylic acid solution may be concentrated by recovering a predetermined proportion of the mixed solvent from the solution by distillation or other means.

From the mixed solvent containing a crude naphthalenedicarboxylic acid dissolved therein, the naphthalenedicarboxylic acid having a high purity is then recovered. This may be accomplished, for example, by any of the following methods: 1) a method in which the mixed solvent solution is cooled to precipitate an amine salt of the naphthalenedicarboxylic acid and the amine is then recovered from the amine salt by heating, thereby to obtain the naphthalenedicarboxylic acid having a high purity; 2) a method in which the mixed solvent solution is cooled to precipitate an amine salt of the naphthalenedicarboxylic acid and the amine salt is then treated with an acid, thereby to obtain the naphthalenedicarboxylic acid having a high purity; and 3) a method in which an acid is added to the mixed solvent solution thereby to obtain the naphthalenedicarboxylic acid having a high purity.

In methods 1 and 2 above, the mixed solvent in which a crude naphthalenedicarboxylic acid has been dissolved is first cooled and the thus-formed precipitate, which is an amine salt of the naphthalenedicarboxylic acid, is recovered by filtration or other means. The temperature to which the mixed solvent solution is cooled is generally lower by at least 30° C., preferably by at least 40° C., than the temperature at which the crude naphthalenedicarboxylic acid was dissolved in the mixed solvent. Specifically, the cooling temperature may be generally in the range of from −30° to 100° C., preferably from −20° to 80° C., more preferably from −20° to 60° C.

In method 1 above, the precipitate separated is then heated to a temperature not lower than the boiling point of the amine which is forming a salt with the naphthalenedicarboxylic acid, thereby to recover the amine. Thus, the naphthalenedicarboxylic acid having a high purity is obtained.

The heating for amine recovery may be conducted at ordinary pressure or a reduced pressure, with or without introduction of an inert gas such as nitrogen or argon.

The temperature to which the precipitate is heated in an atmosphere having a given pressure should not be lower than the boiling point at that pressure of the amine used for crystallization and be lower than the thermal decomposition temperature of the naphthalenedicarboxylic acid (about 280° C.). If the amine used has a boiling point higher than 280° C., heating of the precipitate is conducted at a reduced pressure thereby to lower the boiling point.

Further, it is possible to disperse the separated precipitate into a solvent (other than amines) having a boiling point not lower than the temperature to which the precipitate is to be heated at the pressure of an atomosphere in which the precipitate is to be heated, and heat the dispersion.

As this solvent, any solvent may be used as long as it has a boiling point not lower than the temperature to which the dispersion is to be heated and is not reactive to the amine and the naphthalenedicarboxylic acid. Examples of such a solvent include aliphatic hydrocarbons such as liquid paraffins, aromatic hydrocarbons such as alkylbenzenes, alkylnaphthalenes, and alkylbiphenyls, ethers such as diphenyl ether, and esters.

The naphthalenedicarboxylic acid is insoluble in most solvents and is, hence, solid in the above-enumerated solvents. Therefore, the naphthalenedicarboxylic acid having a high purity can be obtained from the dispersion of the precipitate by heating the dispersion to recover the amine compound and then separating the solid matter from the dispersion medium by filtration or other means.

In methods 2 and 3 above, an acid is added to the precipitate formed by cooling the mixed solvent solution of a crude naphthalenedicarboxylic acid or directly to the mixed solvent solution, thereby to obtain the naphthalenedicarboxylic acid having a high purity.

Examples to the acid for use in method 2 or 3 include aliphatic carboxylic acids such as formic acid, acetic acid, propionic acid, butyric acid, monochloroacetic acid, monobromoacetic acid, trifluoroacetic acid, and trichloroacetic acid; and inorganic acids such as hydrochloric acid, hydrogen bromide, sulfuric acid, nitric acid, phosphoric acid, and perchloric acid. Such an acid may be added as it is or i.n the form of an aqueous solution. However, from the standpoint of easiness of post-treatment, it is preferred to add an aliphatic carboxylic acid having up to 5 carbon atoms, e.g., acetic acid, as it is.

The amount of an acid to be used in method 2 or 3 may be generally in the range of from 0.1 to 10 mol, preferably from 0.3 to 6 mol, per mol of the amine compound contained in the amine salt or in the mixed solvent solution of a crude naphthalenedicarboxylic acid.

Acid treatment of the precipitate, i.e., an amine salt of the naphthalenedicarboxylic acid, formed by cooling the mixed solvent solution can be carried out by adding a predetermined amount of an acid to the precipitate crystals and stirring the resulting mixture at a temperature of generally from 0° to 200° C., preferably from 20° to 150° C., for a period of generally from 0.1 to 4 hours, preferably from 0.3 to 2 hours. Thus, the naphthalenedicarboxylic acid crystallizes out. This acid treatment may be conducted using such a solvent as an alcohol or a ketone. The amount of the acid to be used may be generally in the range of from 0.1 to 100 times by weight, preferably from 0.3 to 50 times by weight, the amount of the naphthalenedicarboxylic acid amine salt.

Since part of the amine compound used for crystallization is adherent to the naphthalenedicarboxylic acid crystals obtained by crystallization and filtration, it is preferable to wash the crystals with an acid.

Examples of the acid for use in washing include aliphatic carboxylic acids such as formic acid, acetic acid, propionic acid, butyric acid, monochloroacetic acid, monobromoacetic acid, trifluoroacetic acid, and trichloroacetic acid and inorganic acids such as hydrochloric acid, sulfuric acid, nitric acid, phosphoric acid, and perchloric acid. Particularly preferred of these is acetic acid. Such an acid may be used either as it is or after being diluted with water, an alcohol, a ketone, or other solvent to an arbitrary concentration.

The amount of the acid to be used for washing the naphthalenedicarboxylic acid crystals obtained by crystallization and filtration may be generally in the range of from 0.5 to 20 times by weight, preferably from 1 to 10 times by weight, the amount of the crystals.

The naphthalenedicarboxylic acid crystals precipitated by the above-described operation were filtered off and dried, thereby to obtain the naphthalenedicarboxylic acid having a high purity.

The filtrate from which naphthalenedicarboxylic acid crystals have been removed by filtration contains impurities and coloring substances. However, the filtrate can be reused repeatedly for crystallization, usually without any particular treatment or, if necessary, after being purified.

Although naphthalenedicarboxylic acids dissolve, in some degree, in DMF, DMAc, DMSO, ethanolamine and its derivatives, and pyridine and its derivatives, they are substantially insoluble in the other organic solvents. Naphthalenedicarboxylic acids, therefore, do not substantially dissolve in amine compounds other than ethanolamine and its derivatives and in alcohols if such solvents are used alone, and do never form a salt with an amine compound. In the case of ethanolamine and its derivatives, although naphthalenedicarboxylic acids are soluble therein in some degree, the solubility changes little with changing temperature and, in addition, crystallization of naphthalenedicarboxylic acids from their solutions in these solvents is impossible because the viscosities of the solutions increase considerably. However, the present inventors found that when an amine compound is used as a solvent in the form of a mixture with an alcohol, the solubility of naphthalenedicarboxylic acids is improved significantly and the naphthalenedicarboxylic acids form salts with the amine compound upon dissolution in the mixed solvent. Since the temperature dependence of the solubility of naphthalenedicarboxylic acids in the mixed solvent is extremely high and the solutions have low viscosities, purification of crude naphthalenedicarboxylic acids by crystallization from solutions thereof in the mixed solvent can be carried out with great ease.

Further, the addition of an acid, e.g., an aliphatic carboxylic acid, to the mixed solvent in which a crude naphthalenedicarboxylic acid has been dissolved is effective in recovering the naphthalenedicarboxylic acid as crystals having a high purity and good color, because the solubility of the naphthalenedicarboxylic acid is reduced considerably by the acid.

As described above, by use of the process of the present invention, a naphthalenedicarboxylic acid having a high purity and good color can be produced efficiently in a high recovery from a crude naphthalenedicarboxylic acid obtained by the oxidation reaction of a di-substituted naphthalene and containing impurities and coloring substances.

The present invention will be explained below in more detail with reference to the following Reference Examples, Examples, and Comparative Examples, but the invention is not construed as being limited to the Examples.

In these examples, the purity of a naphthalenedicarboxylic acid was measured by high-speed liquid chromatography. Further, the color was evaluated in terms of optical density (hereinafter abbreviated as OD), which was determined by dissolving 1 g of the sample in 10 ml of 25% methylamine aqueous solution and measuring the absorbance of the solution at a wavelength of 500 nm using a 10-mm quartz cell.

REFERENCE EXAMPLE 1

Into a 500-ml autoclave made of titanium and equipped with a reflux condenser, gas-introducing tube, raw material feed pump, back pressure regulator, and induction stirrer were introduced 200 g of acetic acid, 9.4 g (37.5 mmol) of cobalt acetate tetrahydrate, 9.2 g (37.5 mmol) of manganese acetate tetrahydrate, 7.4 g (75.0 mmol) of ammonium bromide, and 5.9 g (75.0 mmol) of pyridine. The atmosphere in the autoclave was then replaced with nitrogen and the pressure inside the autoclave was regulated at 30 kg/cm$^2$GP (gauge pressure) with the back pressure regulator. Subsequently, the contents were heated to 200° C., and air was fed at a rate of 4 Nl/min in such a manner that the pressure inside the autoclave was maintained at 30 kg/cm$^2$GP. After the condition inside the autoclave had become stable, 79.6 g (375 mmol) of 2,6-diisopropylnaphthalene was fed continuously over a period of 4 hours. Thereafter, the feeding of air was further continued for 1 hour while the inside of the autoclave was kept at 200° C. and 30 kg/cm$^2$GP.

After completion of the reaction, the autoclave was cooled to room temperature, and the solid precipitate which had separated out was filtered off and washed with 40 g of acetic acid. This precipitate was dried, thereby obtaining 67.2 g of crude 2,6-naphthalenedicarboxylic acid as a pale-brown solid in a yield of 80.6%. The crude compound thus obtained had a purity of 97.2% and an OD of 3.44.

EXAMPLE 1

Into a 200-ml flask were introduced 13.5 g of the crude 2,6-naphthalenedicarboxylic acid obtained in Reference Example 1, 46.5 g of methanol, and 31.0 g of triethanolamine. The contents were then heated at 80° C. to dissolve the crude compound. Subsequently, this solution was passed through a jacketed column packed beforehand with 4 g of active carbon and heated at 68° C., at an LHSV (liquid hourly space velocity) of 1.0 hr$^{-1}$. The recovered solution in an amount of 88.4 g was cooled to room temperature and the crystals thus precipitated were filtered off. As a result, 60 g of a filtrate was obtained.

In a flask were placed 27 g of the crystals obtained above and 40 g of acetic acid. The crystals were washed with the acetic acid at room temperature, subsequently filtered off, and then rinsed with 10 g of acetic acid. The crystals thus cleaned were dried under a reduced pressure, thereby obtaining 10.2 g of purified 2,6-naphthalenedicarboxylic acid. The recovery was 75.6%. The purified compound had a purity of 99.1% and an OD of 0.044.

EXAMPLE 2

In the same manner as in Example 1, 12.0 g of the same crude 2,6-naphthalenedicarboxylic acid was dissolved in 60.0 g of methanol and 15.0 g of triethanolamine and the solution was treated with active carbon. The recovered solution in an amount of 85.0 g was cooled to room temperature and the crystals thus precipitated were filtered off. As a result, 60 g of a filtrate was obtained.

In a flask were placed 12 g of the crystals obtained above and 20 g of acetic acid. The crystals were washed with the acetic acid at room temperature, subsequently filtered off, and then rinsed with 5 g of acetic acid. The crystals thus cleaned were dried under a reduced pressure, thereby obtaining 6.1 g of purified 2,6-naphthalenedicarboxylic acid. The recovery was 50.8%. The purified compound had a purity of 99.3% and an OD of 0,039.

EXAMPLE 3

Into a 200-ml flask were introduced 10.0 g of the crude 2,6-naphthalenedicarboxylic acid obtained in Reference Example 1, 15.0 g of methanol, and 15.0 g of triethylamine. The contents were then heated at 65° C. to dissolve the crude compound. Subsequently, this solution was passed through a jacketed column packed beforehand with 4 g of active carbon and heated at 67° C., at an LHSV of 0.5 hr$^{-1}$. The recovered solution in an amount of 43.9 g was cooled to room temperature and the crystals thus precipitated were filtered off. As a result, 26 g of a filtrate was obtained.

In a flask were placed 17 g of the crystals obtained above and 30 g of acetic acid. The crystals were washed with the acetic acid at room temperature, subsequently filtered off, and then rinsed with 10 g of acetic acid. The crystals thus cleaned were dried under a reduced pressure, thereby obtaining 5.6 g of purified 2,6-naphthalenedicarboxylic acid. The recovery was 56.3%. The purified compound had a purity of 99.6% and an OD of 0.022.

EXAMPLE 4

Into a 200-ml flask were introduced 10.9 g (50mmol) of the crude 2,6-naphthalenedicarboxylic acid obtained in Reference Example 1, 11.0 g of methanol, and 10.6 g (105 mmol) of triethylamine. The contents were then heated on a 80° C. oil bath to dissolve the crude compound. Subsequently, this solution was passed, at an LHSV of 1.0 hr$^{-1}$, through a jacketed column packed beforehand with 4 g of active carbon and heated at 70° C. and, thereafter, 2 g of methanol was further passed through the column and then added to the treated solution. The recovered solution amounting to 31.8 g was cooled to room temperature and the crystals thus precipitated were filtered off. As a result, 12.6 g of a filtrate was obtained.

In a flask were placed 18.8 g of the crystals obtained above. Subsequently, the crystals in the flask were heated at 120° C. with stirring for 2 hours in a stream of nitrogen, thereby obtaining 9.1 g of purified 2,6-naphthalenedicarboxylic acid. The recovery was 84.2%. The purified compound had a purity of 99.5% and an OD of 0.052.

EXAMPLE 5

A crude 2,6-naphthalenedicarboxylic acid solution treated with active carbon was prepared in the same manner as in Example 4. The recovered solution amounting to 32.0 g was cooled to room temperature and the crystals thus precipitated were filtered off. As a result, 12.9 g of a filtrate was obtained.

In a flask were placed 19.0 g of the crystals obtained above. Subsequently, the crystals in the flask were heated at 120° C. with stirring for 2 hours under a reduced pressure of 25 mmHg, thereby obtaining 9.0 g of purified 2,6-naphthalenedicarboxylic acid. The recovery was 83.9%. The purified compound had a purity of 99.7% and an OD of 0.056.

EXAMPLE 6

A crude 2,6-naphthalenedicarboxylic acid solution treated with active carbon was prepared in the same manner as in Example 4. The recovered solution amounting to 32.2 g was cooled to room temperature and the crystals thus precipitated were filtered off. As a result, 13.0 g of a filtrate was obtained.

In a flask were placed 19.3 g of the crystals obtained above and 30 g of a liquid paraffin. Subsequently, the mixture in the flask was heated at 120° C. with stirring for 2 hours under a pressure of 22 mmHg. After the resulting mixture was cooled to room temperature, the crystals were filtered off, rinsed with hexane, and then dried, thereby obtaining 9.2 g of purified 2,6-naphthalenedicarboxylic acid. The recovery was 85.0%. The purified compound had a purity of 99.9% and an OD of 0.051.

COMPARATIVE EXAMPLE 1

Into a 200-ml flask were introduced 1.0 g of the crude 2,6-naphthalenedicarboxylic acid obtained in Reference Example 1 and 60.0 g of methanol. The contents were then heated at 80° C. with refluxing for 4 hours. As a result, however, the crude 2,6-naphthalenedicarboxylic acid remained almost undissolved and, hence, the crude compound was unable to be purified by crystallization.

COMPARATIVE EXAMPLE 2

The same procedures as in Comparative Example 1 were conducted except that 60.0 g of triethylamine was used in place of methanol. As a result, however, the crude 2,6-naphthalenedicarboxylic acid remained almost undissolved and, hence, the crude compound was unable to be purified by crystallization.

COMPARATIVE EXAMPLE 3

The same procedures as in Comparative Example 1 were conducted except that 15.0 g of acetone and 10.0 g of triethanolamine were used in place of methanol. As a result, however, the crude 2,6-naphthalenedicarboxylic acid remained almost undissolved and, hence, the crude compound was unable to be purified by crystallization.

COMPARATIVE EXAMPLE 4

Into a 200-ml flask were introduced 6.0 g of the crude 2,6-naphthalenedicarboxylic acid obtained in Reference Example 1 and 60.0 g of triethanolamine. The contents were then heated at 100° C. for 30 minutes to dissolve the crude compound, and the resulting solution was cooled to room temperature. As a result, however, no crystals separated out. Hence, in order to concentrate the solution, vacuum distillation was performed. However, the solution gelled as a result of the concentration and the crude compound was unable to be purified by crystallization.

COMPARATIVE EXAMPLE 5

A crude 2,6-naphthalenedicarboxylic acid solution was prepared in the same manner as in Comparative Example 4 except that 60.0 g of 20 wt % triethylamine aqueous solution was used in place of triethanolamine. This solution was cooled to room temperature, but no crystals separated out. Thus, the crude compound was unable to be purified by crystallization.

COMPARATIVE EXAMPLE 6

Into a 200-ml flask were introduced 5.0 g of the crude 2,6-naphthalenedicarboxylic acid obtained in Reference Example 1, 27.1 g of DMSO, and 0.4 g of active carbon. The contents were then heated at 120° C. for 30 minutes to dissolve the crude compound. Thereafter, the active carbon was filtered off and rinsed with 9 g of DMSO and the rinsings were added to the filtrate. Subsequently, 28.8 g of DMSO was recovered from the filtrate by vacuum distillation. As a result, the amount of the DMSO remaining in the flask had decreased to 7.0 g, which was 1.4 times by weight the amount of the crude 2,6-naphthalenedicarboxylic acid.

The contents in the flask were then cooled to room temperature, and the 2,6-naphthalenedicarboxylic acid crystals thus precipitated were filtered off, rinsed with 5 g of DMSO, and then dried, thereby obtaining 3.8 g of purified 2,6-naphthalenedicarboxylic acid. The recovery was 75.2%. The purified compound had a purity of 99.8% and an OD of 2.87.

COMPARATIVE EXAMPLE 7

Into a 200-ml flask were introduced 3.0 g of the crude 2,6-naphthalenedicarboxylic acid obtained in Reference Example 1, 74.8 g of DMF, and 0.5 g of active carbon. The contents were then heated at 120° C. for 30 minutes to dissolve the crude compound. Thereafter, the active carbon was filtered off and rinsed with 13 g of DMF and the rinsings were added to the filtrate. Subsequently, 81.6 g of DMF was recovered from the filtrate by vacuum distillation. As a result, the amount of the DMF remaining in the flask had decreased to 6.0 g, which was 2.0 times by weight the amount of the crude 2,6-naphthalenedicarboxylic acid. The contents in the flask were then cooled to room temperature, and the 2,6-naphthalenedicarboxylic acid crystals thus precipitated were filtered off, rinsed with 5 g of DMF, and then dried, thereby obtaining 2.5 g of purified 2,6-naphthalenedicarboxylic acid. The recovery was 85.0%. The purified compound had a purity of 98.5% and an OD of 1.62.

EXAMPLE 7

Into a 100-ml flask were introduced 3.0 g of the crude 2,6-naphthalenedicarboxylic acid obtained in Reference Example 1, 21.0 g of methanol, and 10.0 g of triethanolamine. The crude compound was dissolved in the solvent at room temperature. Subsequently, this solution was passed through a jacketed column packed beforehand with 2.5 g of active carbon and heated at 68° C., at an LHSV of 1.0 hr$^{-1}$. After the whole solution had been passed, a liquid mixture of 15 g of methanol and 5 g of triethanolamine was further passed through the column and then added to the treated solution. Thereafter, 30 g of acetic acid was added to the recovered solution amounting to 53.0 g thereby to precipitate crystals, which were then filtered off.

The crystals obtained above were washed with methanol and then dried, thereby obtaining 2.8 g of purified 2,6-naphthalenedicarboxylic acid. The recovery was 92.3%. The purified compound had a purity of 99.8% and an OD of 0.017.

EXAMPLE 8

A crude 2,6-naphthalenedicarboxylic acid solution was prepared in the same manner as in Example 7 except that 20.0 g of methanol and 6.0 g of triethylamine were used as the solvent. This solution was passed through the same column as that used in Example 7 at an LHSV of 0.5 hr$^{-1}$. Thereafter, a liquid mixture of 10 g of methanol and 3 g of triethylamine was further passed through the column and then added to the treated solution. Subsequently, 30 g of acetic acid was added to the recovered solution amounting to 41.0 g thereby to precipitate crystals, which were then filtered off.

The crystals obtained above were washed with methanol and then dried, thereby obtaining 2.5 g of purified 2,6-naphthalenedicarboxylic acid. The recovery was 84.0%. The purified compound had a purity of 99.5% and an OD of 0.015.

REFERENCE EXAMPLE 2

Into a 100-ml flask were introduced 3.0 g of the crude 2,6-naphthalenedicarboxylic acid obtained in Reference Example 1, 25.0 g of methanol, 10.0 g of triethanolamine, and 0.5 g of active carbon. The contents were then stirred at 80° C. for 1 hour. The resulting mixture was cooled to room temperature and the active carbon was then filtered off. Subsequently, 63.0 g of acetone was added to the filtrate and the crystals thus precipitated were recovered by filtration. To the thus-obtained crystals was added 46.0 g of acetone. This mixture was heated to clean the crystals. After cooling, the mixture was subjected to filtration, followed by drying, thereby obtaining 4.8 g of pale-yellow crystals. The crystals thus obtained had a purity of 44.6% and contained a large amount of triethanolamine.

While the invention has been described in detail and with reference to specific embodiments thereof, it will be apparent to one skilled in the art that various changes and modifications can be made therein without departing from the spirit and scope thereof.

What is claimed is:

1. A process for producing a naphthalenedicarboxylic acid which comprises dissolving a crude naphthalenedicarboxylic acid in a mixed solvent comprising an amine compound and an alcohol and conducting crystallization, said crude naphthalenedicarboxylic acid being one obtained by the oxidation of a di-substituted naphthalene, wherein the proportion of the amine compound to the alcohol in the mixed solvent is in the range of from 1:99 to 99:1 by weight, and wherein the mixed solvent is used in an amount from 0.5 to 100 times by weight the amount of the crude naphthalenedicarboxylic acid.

2. A process as claimed in claim 1, wherein said alcohol is an aliphatic monohydric alcohol.

3. A process as claimed in claim 1, wherein the dissolution of the crude naphthalenedicarboxylic acid is conducted at a temperature of from 0° to 350° C.

4. A process as claimed in claim 1, wherein the crystallization is conducted after the solution prepared by dissolving the crude naphthalenedicarboxylic acid is treated with active carbon.

5. A process as claimed in claim 1, wherein the di-substituted naphthalene is a 2,6-substituted naphthalene or a 2,7-substituted naphthalene.

6. A process as claimed in claim 1, wherein the amine compound is an alkylamine having up to 30 carbon atoms.

7. A process for producing a high-purity naphthalenedicarboxylic acid which comprises dissolving a crude naphthalenedicarboxylic acid in a mixed solvent comprising an amine compound and an alcohol and then cooling the resulting solution to a temperature lower by at least 30° C. than the temperature at which the crude naphthalenedicarboxylic acid was dissolved in the mixed solvent, thereby to precipitate an amine salt of the naphthalenedicarboxylic acid, wherein the proportion of the amine compound to the alcohol in the mixed solvent is in the range of from 1:99 to 99:1 by weight, and wherein the mixed solvent is used in an amount from 0.5 to 100 times by weight the amount of the crude naphthalenedicarboxylic acid.

8. A process as claimed in claim 7, wherein the precipitation is conducted at a temperature of from −30° to 100° C.

9. A process as claimed in claim 7, which further comprises heating the precipitated amine salt to a temperature not lower than the boiling point of the amine thereby to obtain the naphthalenedicarboxylic acid.

10. A process as claimed in claim 7, which further comprises adding an acid to the precipitated amine salt thereby to obtain the naphthalenedicarboxylic acid.

11. A process as claimed in claim 10, wherein the acid is added in an amount of from 0.1 to 10 mol per mol of the amine salt.

12. A process as claimed in claim 10, wherein the acid to be added is an aliphatic carboxylic acid.

13. A process for producing a high-purity naphthalenedicarboxylic acid which comprises dissolving a crude naphthalenedicarboxylic acid in a mixed solvent comprising an amine compound and an alcohol and then adding an acid to the resulting solution thereby to precipitate the naphthalenedicarboxylic acid.

14. A process as claimed in claim 13, wherein the acid is added in an amount from 0.1 to 10 times by weight the amount of the amine contained in the solution.

15. A process as claimed in claim 13, wherein the precipitation is conducted at a temperature of from 0° to 40° C.

16. A process as claimed in claim 13, wherein the acid is an aliphatic carboxylic acid.

* * * * *